(12) United States Patent
Zimmermann

(10) Patent No.: US 7,010,153 B2
(45) Date of Patent: Mar. 7, 2006

(54) TOOTH IDENTIFICATION DIGITAL X-RAY IMAGES AND ASSIGNMENT OF INFORMATION TO DIGITAL X-RAY IMAGES

(75) Inventor: Jürgen Zimmermann, Blebesheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 89 days.

(21) Appl. No.: 10/644,991

(22) Filed: Aug. 21, 2003

(65) Prior Publication Data

US 2004/0086160 A1 May 6, 2004

Related U.S. Application Data

(63) Continuation of application No. PCT/DE02/00634, filed on Feb. 21, 2002.

(51) Int. Cl.
G06K 9/00 (2006.01)

(52) U.S. Cl. .................................. 382/132; 382/305
(58) Field of Classification Search ............... 382/128, 382/132, 305, 306; 707/100, 102, 103 R, 707/103 Y, 103 Z, 104.1; 705/2
See application file for complete search history.

(56) References Cited

U.S. PATENT DOCUMENTS

| | | | | |
|---|---|---|---|---|
| 4,813,060 A | | 3/1989 | Heubeck et al. ............... 378/39 |
| 4,847,881 A | | 7/1989 | Heubeck ...................... 378/38 |
| 5,235,510 A | * | 8/1993 | Yamada et al. ........ 364/413.02 |
| 5,511,106 A | | 4/1996 | Doebert et al. ............. 378/146 |
| 5,513,252 A | | 4/1996 | Blaschka et al. .......... 378/98.8 |
| 5,721,851 A | * | 2/1998 | Cline et al. ................. 395/349 |
| 5,740,267 A | * | 4/1998 | Echerer et al. ............. 382/132 |
| 5,742,700 A | * | 4/1998 | Yoon et al. ................. 382/132 |
| 5,807,256 A | * | 9/1998 | Taguchi et al. ............. 600/425 |
| 6,289,074 B1 | * | 9/2001 | Arai et al. ....................... 378/4 |
| 2001/0051881 A1 | * | 12/2001 | Filler ............................. 705/3 |
| 2002/0178032 A1 | * | 11/2002 | Benn et al. .................... 705/2 |

FOREIGN PATENT DOCUMENTS

DE 197 35 112 A1 2/1999

OTHER PUBLICATIONS

Burdea et al., "Real Time Tooth Position Measurements for Digital Dental Subtraction Radiography," Proc. Int. Conf. of the IEEE Engineering in Medicine and Biology Society, Nov. 1990, pp. 2078-2079.*
White et al., "Digital Imaging: A Vision for the Future," Online paper from www.dent.ucla.edu/sod/depts/oral_rad/VisionStatement.html, as archived on Jan. 29, 1999 at www.archive.org, 3 pages.*
VixWin 2000 Plug In & NetzWerk, Aug. 7, 2003 Rontgen, Jan. 22, 2003.

* cited by examiner

*Primary Examiner*—Andrew W. Johns
(74) *Attorney, Agent, or Firm*—Dykema Gossett PLLC

(57) ABSTRACT

A method and device for identifying objects, especially teeth, on a digitized X-ray picture, by using image processing algorithms to localize areas containing the object by segmenting and/or edge detection, these areas being computationally linked with parameters of the X-ray unit and, optionally, with patient-heightened specific parameters. Another method and device for assigning information to objects, especially teeth, determined in a digitized X-ray picture or in a schematic representation, includes a first step detecting the digitized X-ray image for the schematic representation, a second step in which a determination of objects manually or automatically ensues in the event these objects have not yet been determined, a third step selecting the object for which additional information should be stored, retrieved or deleted, and a fourth step in which a reference that is stored is followed for a query operation to determine the information displayed by using such reference.

16 Claims, 5 Drawing Sheets

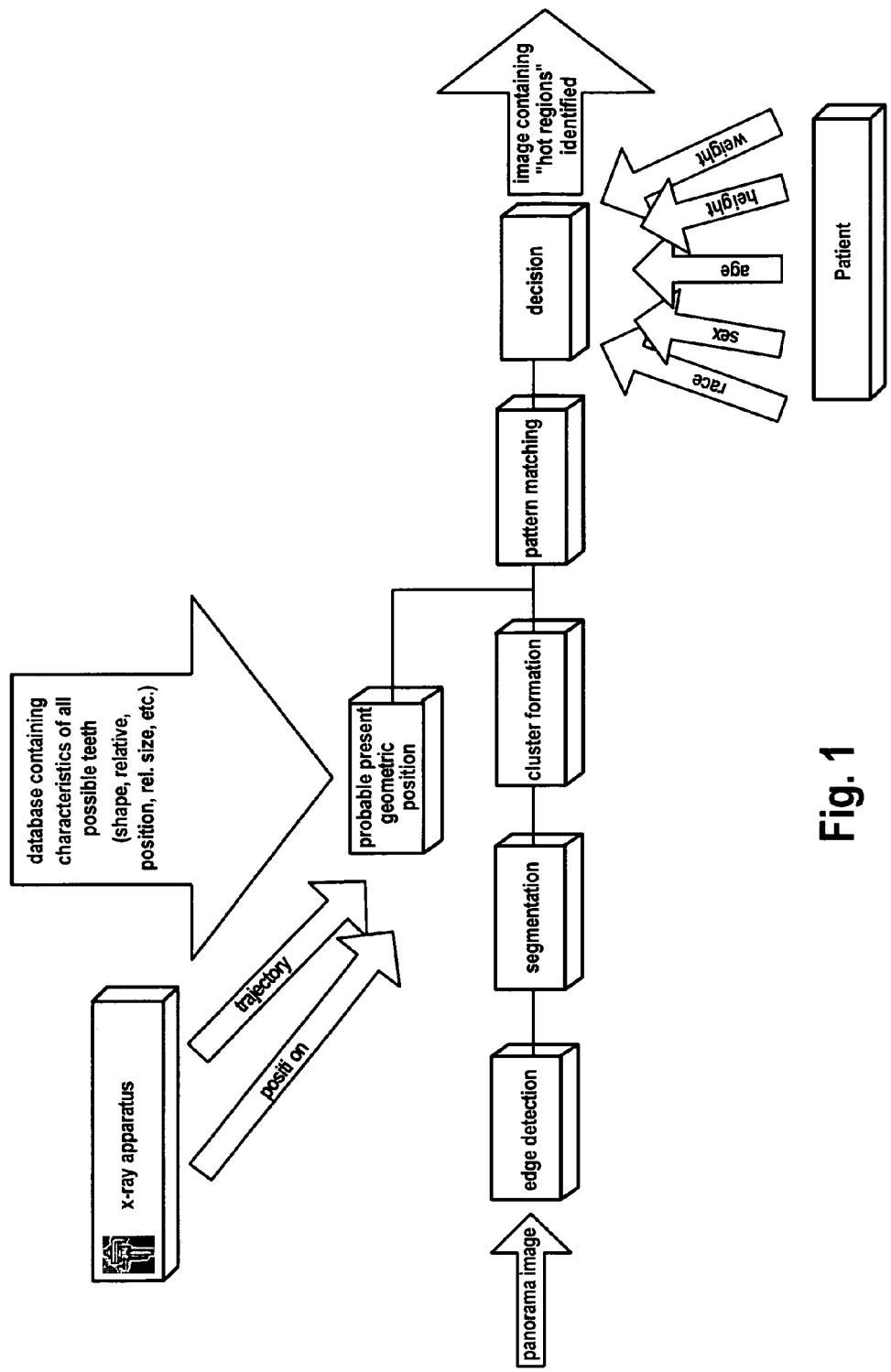

TOOTH IDENTIFICATION DIGITAL X-RAY IMAGES AND ASSIGNMENT OF INFORMATION TO DIGITAL X-RAY IMAGES

CROSS REFERENCE TO RELATED APPLICATION

This is a continuation of International Application PCT/DE02/00634 filed Feb. 21, 2002, which designated the U.S. All priorities are claimed.

TECHNICAL FIELD

The invention relates to a method of identifying objects, particularly teeth, in a digitized X-ray image and to a system for effecting same. The invention also relates to a method of assigning information to objects, particularly teeth, specified in a digitized X-ray image or a schematic diagram and to a system for effecting same.

BACKGROUND OF THE INVENTION

X-ray apparatus for making panoramic radiograms and individual images therefrom is disclosed in DE 3 545 509 (U.S. Pat. No. 4,847,881) and DE 3 545 493 (U.S. Pat. No. 4,813,060). Digital X-ray images for panoramic radiograms and cephalometric images are disclosed in EP 0 632 994 (U.S. Pat. No. 5,511,106). The production of digital intraoral images using an intraoral sensor is disclosed in EP 0 643 901 (U.S. Pat. No. 5,513,252). The features disclosed in these documents are incorporated in this application by reference.

Many diagnostic methods refer to individual details such as individual teeth, of which the existence, shape, and position differ individually. Diagnostics and documentation are hampered by the fact that the users are forced, when performing further actions, to resort not to individual but to general diagrams such as the standard tooth scheme on the health insurance certificate.

When making automated series of radiograms is it necessary to previously inform the operating program as to which teeth are to be inspected.

The solution to this problem is at present either inadequate or complicated since it is only possibly to select either entire conventional fixed groups of teeth or only individual teeth. In all cases the contact with reality is lost, since the user must leave his usual environment, eg, a real dentition radiogram.

Panoramic radiograms serve the purpose of quickly providing an overview of the general condition of the dentition. Such images can provide information without the need for other, eg, intraoral, X-ray images. However, these findings refer not to the entire image but to a specific displayed object, eg, a certain tooth. This thus gives rise to several findings referring to one image and to which, for example, the individual teeth are assigned. Acquisition thereof is complicated, because as a rule the user no longer has direct contact with his accustomed environment of a panoramic image.

It is an object of the present invention to provide an individual tooth scheme and to assign information thereto.

SUMMARY OF THE INVENTION

This object is achieved by methods and systems as defined in the independent claims below.

A particular solution is provided by a method of identifying objects, particularly teeth, in a digitized X-ray image. In order to afford maximum accuracy of recognition, the areas depicting the possible object(s) are specified by segmentation and/or edge detection of the X-ray image using image-processing algorithms and these areas are, for further specification, linked by computation to parameters of the X-ray apparatus used for making the X-ray image.

The method can in addition be developed such that the apparatus-specific parameters are linked to parameters of a non-patient-related tooth data bank, in order to obtain probable actual geometrical positions over the areas depicting the possible object(s). Another possibility is to carry out pooling (clustering) of recognized areas prior to linking to the apparatus-specific parameters. Furthermore, patient-specific parameters are additionally linked by computation for further specification of areas depicting the possible object(s). These additional parameters are position data, trajectories, and starting and finishing points of the X-ray apparatus. The position data and trajectories can provide information on whether the tooth is a premolar or an incisor. In conjunction with statistical and stochastic data, the size of this tooth can be determined, by which means pattern recognition is greatly simplified. Furthermore it is important to have information on the gray scales of the image. This information can lead to better recognition of edges. Thus it is possible to differentiate between flat tooth areas and other areas.

Furthermore, computation can involve information concerning the patients. Information as to which teeth are no longer present or which teeth have been replace, make it possible for the pattern recognition to use particularly elaborate recognition methods in these areas or, respectively, to carry out no pattern recognition. Furthermore anatomic patient characteristics may also be taken into account. Information concerning the race, age, sex, size, and weight can provide statistical conclusions on the jaw shape and the size and arrangement of the teeth.

In the case of recognition errors, the user should have the possibility of interactively determining which areas are to be assigned to a tooth and which not. To this end, the user is presented with proposals on the recognized objects, which he can confirm or alter interactively. The user has the opportunity to determine the size of an object, for example by manually drawing in polygons.

The gathered information on the objects is stored separately in a database. The information is preferably not directly integrated in the drawing. For reasons of efficiency it is preferred that the information on the objects be stored separately. In this way, the images can be used for other purposes without unwanted markings being visible in the image.

The invention also relates to a system for the identification of objects, particularly teeth, in a digitized X-ray image. This system has input and output devices for interactive control. These input and output devices are preferably a keyboard or pointing device and a display monitor. When correction is necessary, the pointing device can be used to specify the individual areas that depict objects.

Another component of the system is a processing unit, which has access to the digitized X-ray image and to apparatus-specific information of the X-ray apparatus and which delimits the object in the digitized X-ray image on the basis of this information and also by segmentation and/or edge detection. This processing unit is preferably a known processor capable of specifying the individual objects in the X-ray image on the basis of the aforementioned method. The procedure described in the method is carried out entirely by the processor.

The processing unit can, in addition, have access to a non-patient-related tooth data bank and/or patient-specific information. The processing unit can also comprise means for clustering the areas existing after segmentation and/or edge detection.

Thus means may be provided for submitting proposals to the user, which can be interactively accepted, rejected, or modified.

A computer interface to the X-ray apparatus makes it possible to access apparatus-specific data. These data preferably include position data, trajectories, starting and finishing points, color scales, and/or color matchings of the X-ray apparatus, which can be included in the computation as already described above.

The anatomic patient characteristics such as race, age, sex, size, and weight are placed in a data bank. The system accesses this data bank and evaluates it in the manner already described according to preferably statistical data. Should information on the actual mass and sizes of teeth be present, this will naturally be preferably taken into account.

The system is preferably in the form of a PC and has a known serial, parallel, bus-type, or network interface connecting to the X-ray apparatus. The process running in this system is preferably controlled by software. A system as defined in any one or more of the preceding claims, characterized in that the system is a PC controlled by software.

Another component of the present invention is a system which assigns information to recognized objects. This system can be based on the aforementioned systems or methods. However, the system may also be used separately if objects are already present. This involves a system for the assignment of information to objects. These objects are preferably teeth specified in a digitized X-ray image.

The system has input and output devices for interactive control of the system. These devices are preferably keyboards, pointing devices, and display monitors. The X-ray images are filed in a first storage area. This is preferably a container for a large number of digitized X-ray images. Information labeling objects in the X-ray image are also filed in addition to these X-ray images. The object-labeling information is intended to determine the two-dimensional or, optionally, the three-dimensional size of the object in the image. Preferably, separate data structures are used which depict the object in the X-ray image by two-dimensional or multidimensional polygons. This information is laid over the original X-ray image during image build-up. However, it is conceivable that this information may be integrated in the X-ray image itself.

In a second storage area, the information concerning the objects is stored. This information can be text information or image information. Thus it is conceivable that an image of a detail will be stored in higher resolution than additional information. Another possibility consists in providing an indication, by graphical marking, as to in what areas treatment is necessary or has already been carried out. It is likewise possibly to assign several types of information to an object.

Furthermore, references between the objects and the information are stored. These references are preferably pointers or index fields which produce logical links between the objects and the information.

A processing unit controls the operations APPLY, DELETE, and ACCESS. The operations are preferably initiated by the user with the aid of the input and output devices. Thus the processing unit controls access to the different storage areas.

These storage areas are preferably only logically different storage areas. Physically, it can be a coherent storage area.

The use of a physical and logical storage area for the image information, the object information and the additional information is possible but not particularly advantageous, since flexibility is lost.

In order to improve working with the system, the objects are optically high-lighted on the output device. If selectable information should be present, this is characterized graphically by some other feature.

The use of references makes a hierarchical arrangement of information possible. The user can thus move from a panoramic image to images of details and impart information at each level.

A system is advantageous in which the references are in the form of links either directly on the object and/or directly on the information and/or are managed separately.

In a preferred embodiment, the system is a PC equipped with a display monitor, the information being available via pop-up menus. These pop-up menus are shown in the form of pop-up windows appearing when an object is activated by the user. The pop-up menu enables the user to decide whether he would like to file new information or whether he wishes to view information already present.

The further information preferably comprises diagnostic and/or treatment information and/or other X-ray images, particularly of details.

In a preferred embodiment the system has a computer interface to an X-ray apparatus. Via this computer interface, information from the X-ray apparatus is transferred to the system in the form of X-ray images, which are saved to the first or third storage area. If the user has already specified an object from the outset, a reference to this object can likewise be immediately saved to the fourth storage area. The new X-ray image is immediately assigned to an existing X-ray image or a selected partial area thereof and provided with a corresponding reference. Thus a hierarchical arrangement is readily obtained and can optionally extend over several levels.

If no object should as yet have been specified, the system provides means permitting manual selection of a certain area in the X-ray image.

The system preferably has the functionality of a data bank system.

Preferably, the objects are recognized by a system and method described above. A combination of systems is thus conceivable.

Another feature of the present invention is a method of assigning information to objects, particularly teeth, which have been specified in a digitized X-ray image. In a first step, the digitized X-ray image is made. In a second step, the objects are manually or automatically specified. This step is only necessary, however, when the objects have not already been specified. In a third step, the object is selected for which more information is to stored, fetched, or deleted.

Probably the most frequent operation is the interrogation operation for calling information from the data bank. A reference is followed which has been saved in relation to the object, which reference makes it possible to determine the information to be shown.

In the case of a deleting operation, the reference is again followed which has been saved in relation to the object. This reference and any information are then deleted. Information is only deleted when it is referenced by only one object. It may happen that a number of objects reference a single item of information. If, in such a case, the information were deleted, there would be no information for at least one object. In the case of a storage operation, an object is selected and the storage area for the information provided. Furthermore, a storage area for the reference is provided, so that the new information and the corresponding reference can be saved to these storage areas.

It is likewise conceivable that, following specification of the object, digital images are received from the X-ray apparatus, which images are automatically assigned to the particular object. In this case an adequate amount of storage space is allocated for acceptance of the information.

In a preferred embodiment, the information is in the form of graphical tags which can be placed over the images as overlays. In this way it is possible to look at detailed information not visible in the images and to subsequently refine and edit the same.

When objects are to be spread over other areas, the method offers the possibility of specifying areas of the objects in which information can be assigned.

Access to information is preferably effected via pop-up menus which can be made to appear for each of the individual objects.

The processes are preferably controlled by means of software running on a known PC. Furthermore, a data medium may be provided which has a data structure which, following loading, carries a method as defined in one or more of the following method claims into effect.

Other advantageous embodiments are defined in the subclaims.

BRIEF DESCRIPTION OF THE DRAWINGS

A detailed description follows with reference to the drawings, in which:

FIG. 1 shows, diagrammatically, information from an x-ray apparatus and the patient to be used following image recognition;

WORKING EXAMPLE

FIG. 1 shows diagrammatically what information from the X-ray apparatus and the patient can be used following image recognition by edge detection and segmentation. If edges and segments have been found, the attempt is made to group the recognized areas and edges by clustering. In order to identify the corresponding tooth, these groups are compared with tooth shapes of a non-patient-related data base while taking into consideration the instrument parameters, further processing then being carried out while taking into consideration the patient-dependent parameters. As a result, an X-ray image is shown which is specified and divided up by corresponding areas, ie objects. These areas stand for the recognized teeth. Such an area is shown in FIGS. 2a, 2b.

Figure 2A:
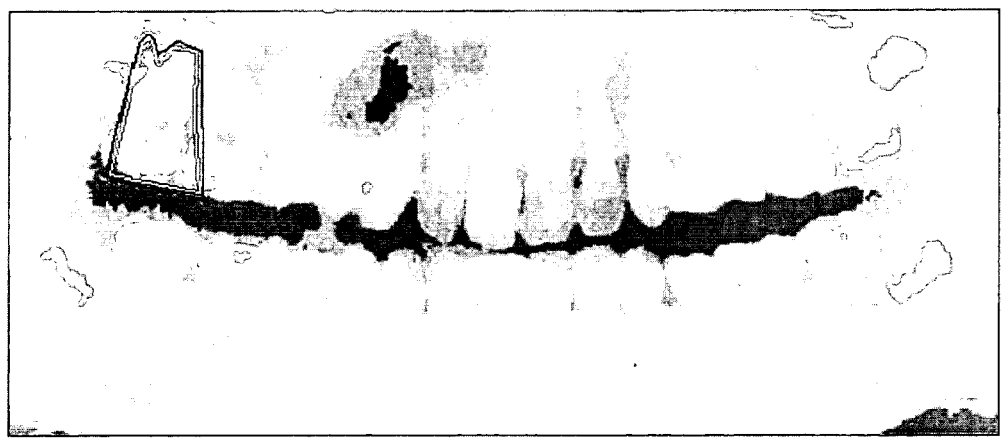
FIG. 2A shows a recognized tooth depicted by an appropriate frame.

FIG. 2a shows a recognized tooth, for which information can be saved. The recognized tooth is depicted by an appropriate frame.

Figure 2B:
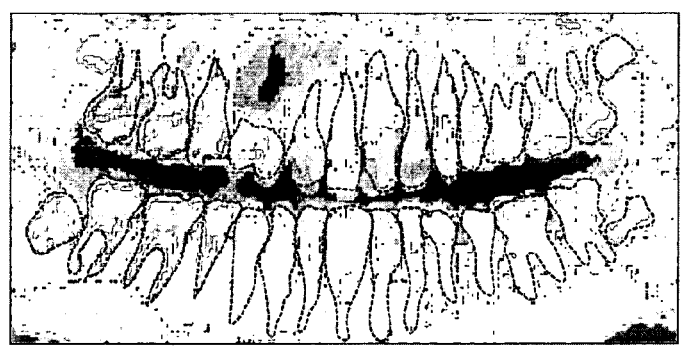
FIG. 2B is a view similar to FIG. 2A.

In FIG. 2b, a group of teeth in the left half of the image has been selected by a mouse click, as a result of which their contours are shown high-lighted. They are teeth in the top row and the bottom row. Information can now be assigned to the teeth thus selected. If, however, too many teeth have been selected, for example, or if it is desired to shift the sensor position a little, or if some of the selected teeth are unimportant, since, although visible, they are not involved in the diagnosis, selection or deselection of one or more teeth may be effected, eg, by conventional mouse actions such as a single or double click, marking an area, etc. directly over the selected areas of the background image. In particular, it is necessary, in the case of a series of radiograms, to previously specify, in the operating program, the individual teeth to be inspected.

Figure 3:
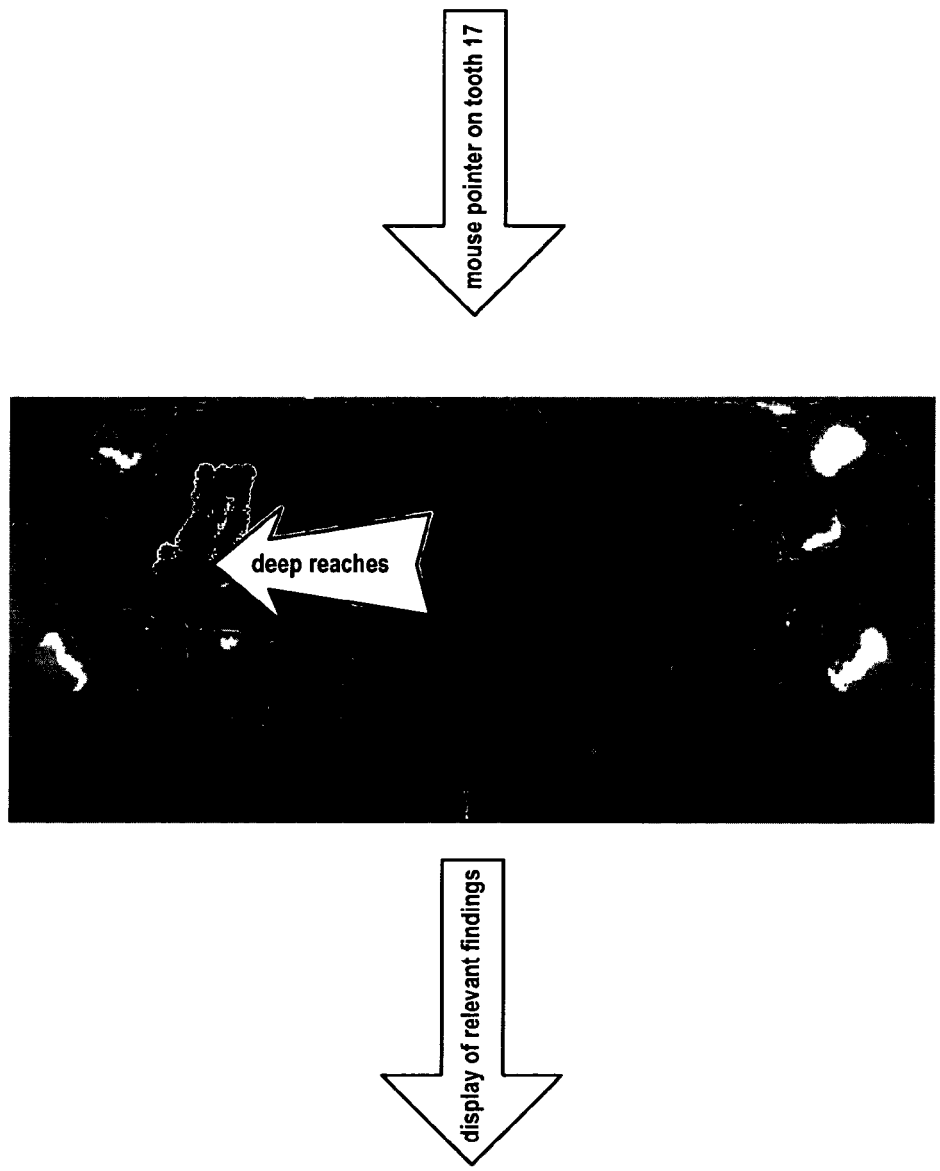
FIG. 3 shows a possible mode of representation of information that has been assigned to objects.

FIG. 3 shows a possible mode of representation of information that has been assigned to objects. In the present case caries is involved. This information is always indicated when the mouse pointer is moved across the corresponding tooth. Other modes of representation are also conceivable, however, particularly the use of small graphical symbols indicating that further information is available for this object.

Figure 4A:
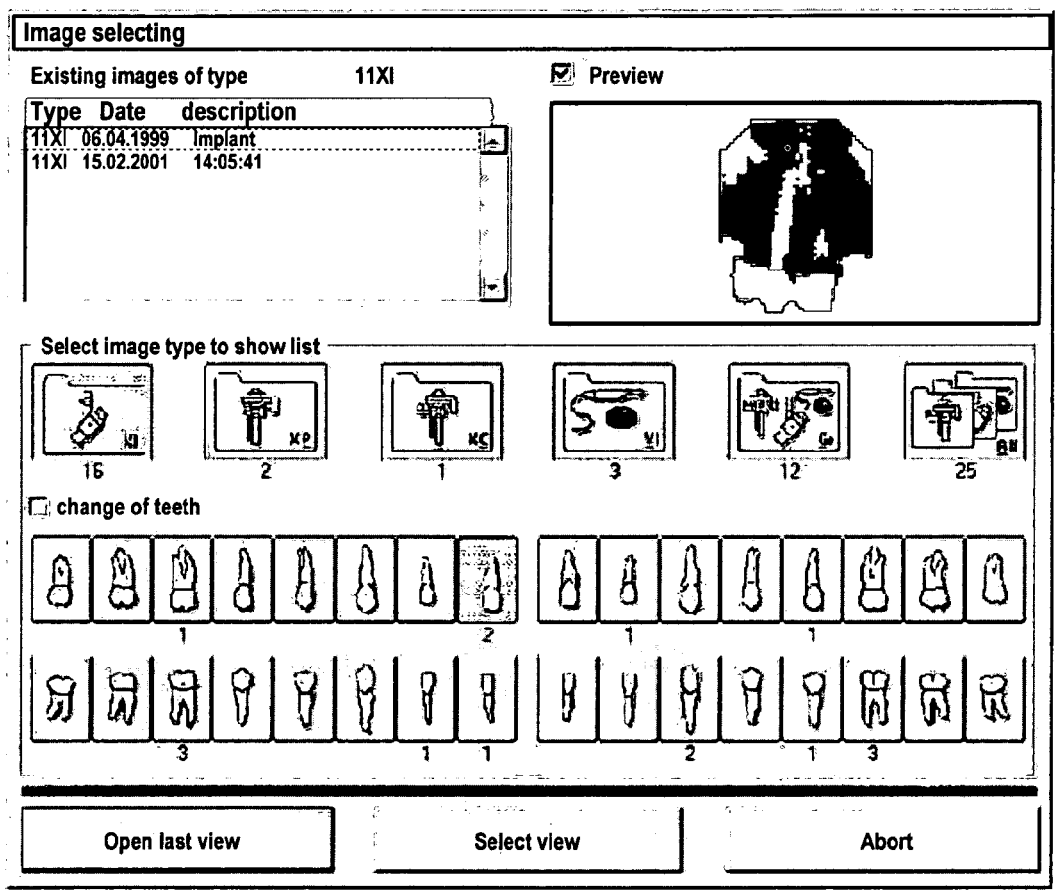
FIGS. 4A and B show a possible method of managing digital x-ray images.
Figure 4B:
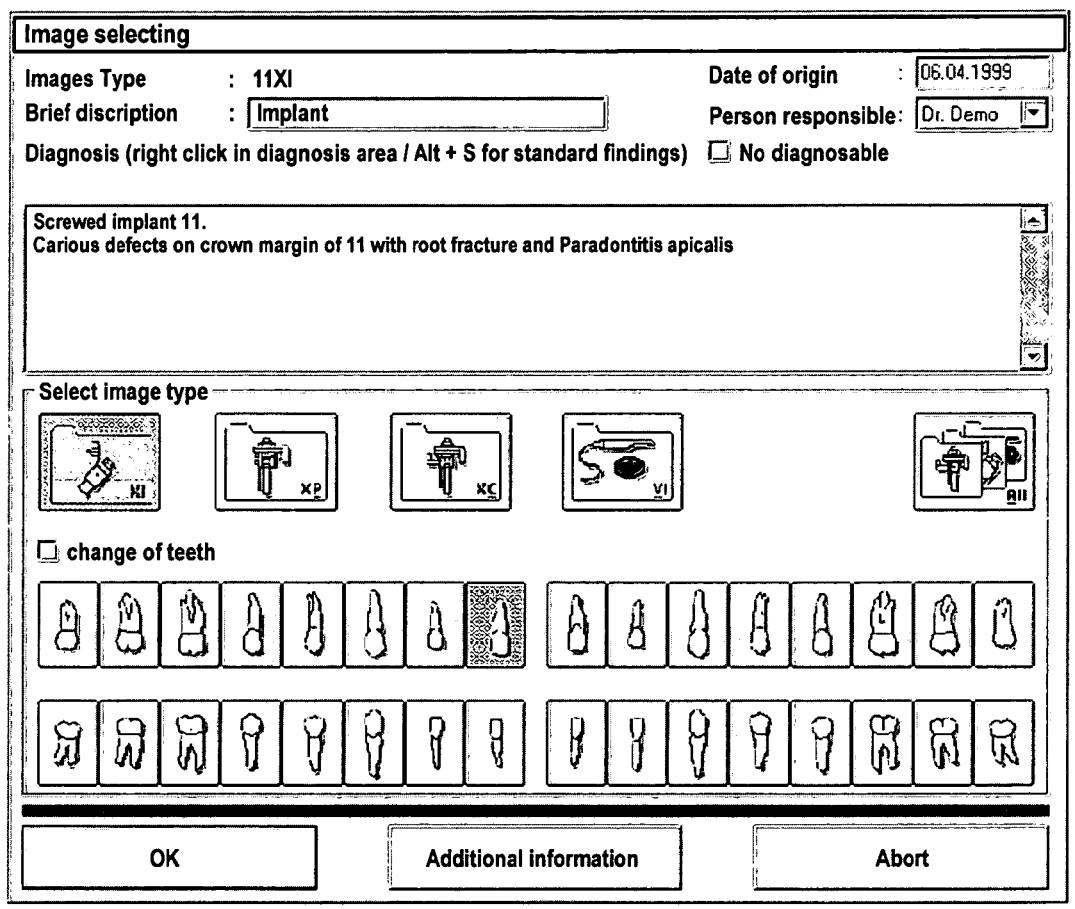

FIGS. 4a and 4b show a possible method of managing digital X-ray images. In this case a corresponding X-ray image is assigned to each tooth, wherever present. This assignment can naturally only take effect when corresponding images are present. FIGS. 4a and 4b show the possibility that the objects need not be restricted to an X-ray image but can alternatively be illustrated in a schematic diagram.

The method can be set down in the form of a software program as defined in any one or more of the following method claims. A data medium can contain a data structure that is capable of running on a computer to carry a method into effect such as is defined in one or more of the following method claims.

What is claimed is:

1. A system for assigning information to objects, including teeth, which are specified in one of a digitized X-ray image and a schematic diagram, comprising
    an input and output device for interactive control of the system,
    a storage area, in which the X-ray image or the schematic diagram is placed, object-labelling information being assigned to the X-ray images or the schematic diagram,
    a second storage area, in which information concerning the objects is placed, references between the objects and the object-labelling information being stored,
    a processing unit which controls accepting, deleting, and/or accessing operations in the storage areas and which manages references, said operations being preferably initiated via the input device and displayed on the output device.

2. A system as defined in claim 1, wherein the output device is capable of showing the objects optically highlighted such that the objects can be further selected in order to retrieve the saved information.

3. A system as defined in claim 2, wherein the output device enables, access to further branched information, if present, when a object is selected.

4. A system as defined in claim 1, wherein the second storage area enables the references to be managed in the form of links positioned either directly near the object and/or directly near the information and/or to be managed separately.

5. A system as defined in claim 1, wherein the output device comprises a visual display unit and the further information is capable of being displayed in one of an automatically opening display field including a pop-up window and the further information leads to a new screen build-up.

6. A system as defined in claim 5, wherein the further information comprises one of diagnostic and treatment information and other X-ray images, including of details.

7. A system as defined in claim 1, further comprising a computer interface to an X-ray apparatus, which transmits, via the computer interface, information in the form of data for representation as X-ray images, information in the form of data being deposited in a third storage area and a reference to an object being saved to a fourth storage area.

8. A system as defined in claim 7, wherein the information in the form of data is capable of being hierarchically arranged over a plurality of levels.

9. A system as defined in claim 1, further comprising means allowing for manual specification of objects by selection of a specific area of the X-ray image.

10. A system as defined in claim 1, further comprising a functionality of a data bank system.

11. A system as defined in claim 1, further comprising a system for identification of objects, including teeth, in a digitized X-ray image, said system for identification of objects comprising means for specifying the areas depicting the object, using image-processing algorithms, by one of segmenting and edge detection of the X-ray image, and that these areas are, for further specification of said areas linking, linked by computation to those image parameters of the X-ray apparatus which are used for making the X-ray image.

12. A method of assigning information to objects, including teeth, which have been specified in one of a digitized X-ray image and a schematic diagram representation, comprising a first step, in which the one of the digitized X-ray image and the schematic diagram is made, a second step, in which specification of the objects, if not already specified, is carried out one of manually and automatically, a third step, in which one of the objects is selected for which further information is to be saved, accessed, or deleted, and a fourth step, in which a) when an interrogation operation is carried out, a reference is followed which has been deposited in relation to the object, which reference is used to determine what information is to be shown, b) when a deleting operation is carried out, a reference is followed which has been deposited in relation to the object, which reference and/or the information is deleted, c) when a storage operation is carried out, an object is selected, a storage area for the information is allocated, and a storage area for the reference is allocated, in order that the new information and the corresponding reference can be saved to these storage areas.

13. A method as defined in claim 12, wherein following specification of the object, data for making digital images are received from the X-ray apparatus, which data are automatically assigned to the specified object.

14. A method as defined in claim 12, wherein the information is in the form of graphical markings which can be placed over the images as an overlay.

15. A method as defined in claim 12, wherein areas of the objects can be specified to which information can be assigned.

16. A method as defined in claim 12, wherein pop-up menus relating to the individual objects can be accessed.

* * * * *